(12) United States Patent
Cuppoletti

(10) Patent No.: US 8,361,809 B2
(45) Date of Patent: Jan. 29, 2013

(54) METHODS FOR IONOPHORICALLY SCREENING PORE FORMING BACTERIAL PROTEIN TOXINS AND RECEPTORS

(76) Inventor: John Cuppoletti, Cincinnati, OH (US)

( * ) Notice: Subject to any disclaimer, the term of this patent is extended or adjusted under 35 U.S.C. 154(b) by 0 days.

(21) Appl. No.: 13/368,861

(22) Filed: Feb. 8, 2012

(65) Prior Publication Data

US 2012/0142044 A1 Jun. 7, 2012

Related U.S. Application Data

(62) Division of application No. 11/832,868, filed on Aug. 2, 2007, now Pat. No. 8,148,172.

(60) Provisional application No. 60/834,968, filed on Aug. 2, 2006.

(51) Int. Cl.
*C12M 1/00* (2006.01)
*C12M 1/34* (2006.01)
*G01N 33/543* (2006.01)

(52) U.S. Cl. ............... 436/518; 436/519; 435/287.3; 435/289.1; 428/304.4

(58) Field of Classification Search .............. None
See application file for complete search history.

(56) References Cited

U.S. PATENT DOCUMENTS 6,387,614 B1 * 5/2002 Cheng et al. ............... 435/4
6,423,502 B2 * 7/2002 Bulla ........................ 435/7.21

FOREIGN PATENT DOCUMENTS

WO  WO 2005022136 A1 * 3/2005

OTHER PUBLICATIONS

Jeon et al. (2006, available online Dec. 9, 2005), J. American Chemical Society, vol. 128, pp. 42-43.*

* cited by examiner

*Primary Examiner* — Christine J Saoud
*Assistant Examiner* — Jegatheesan Seharaseyon
(74) *Attorney, Agent, or Firm* — Dinsmore & Shohl LLP

(57) ABSTRACT

One embodiment of the present invention is directed to methods for ionophorically screening pore forming bacterial protein toxins and receptors for insect toxicity. The method includes: a) forming a membrane comprising a lipid and an insect receptor, b) contacting the membrane with the pore forming bacterial protein toxin and an ion solution, and c) measuring ion flow through the membrane. Also provided are a method and kit for determining the amount of live pore forming bacterial toxin protein in a sample.

6 Claims, 9 Drawing Sheets

METHODS FOR IONOPHORICALLY SCREENING PORE FORMING BACTERIAL PROTEIN TOXINS AND RECEPTORS

CROSS-REFERENCES TO RELATED APPLICATIONS

This application is a divisional of pending U.S. application Ser. No. 11/832,868, filed Aug. 2, 2007, and claims priority under 35 U.S.C. §119(e) to Provisional Application No. 60/834,968 which was filed on Aug. 2, 2006, each of which is incorporated herein by reference.

GOVERNMENT INTERESTS

This invention was made, at least in part, with funds from the U.S. Government, awarded through MURI grant number DAAD 19-0201-0227 ARMY. The U.S. Government, therefore, has certain acknowledged rights to the invention.

FIELD

The present invention is directed to methods for ionophorically screening pore forming bacterial protein toxins and receptors.

BACKGROUND

Bacterial toxins have long been known to exist. They are nearly always proteins that cause disease by contact or by interacting with molecules in the body. The toxins that interact with the body often interact first with cell membranes through receptor recognition. In fact, many bacterial toxins will bind with the receptor to form a gateway through which the toxins can move across the lipid membranes of the cell. In fact, bacterial toxins are one of the few molecules that can accomplish such a feat. Once bound to the receptor, the bacterial toxin will either interact with the cell membrane to inject material into the cell or it will form a pore to release cell nutrients or kill the cell. More than one-third of bacterial toxins are of the pore forming type. Current assays for screening of such bacterial toxins require the use of living animals and thus are slow, laborious, time consuming, and expensive. Therefore, there is a need in the art for new, less expensive and time consuming ways to screen for pore forming bacterial protein toxins and receptors.

SUMMARY

One embodiment of the present invention is directed to methods for ionophorically screening pore forming bacterial protein toxins and receptors. The method includes: a) forming a membrane comprising a lipid and a receptor, b) contacting the membrane with the pore forming bacterial protein toxin and an ion solution, and c) measuring ion flow through the membrane.

Another embodiment of the present invention is directed to methods for ionophorically screening pore forming bacterial protein toxins and receptors for insect toxicity. The method includes: a) forming a membrane comprising a lipid and an insect receptor, b) contacting the membrane with an ion solution and a pore forming bacterial protein toxin, and c) measuring ion flow through the membrane.

An additional embodiment is directed toward methods for determining the amount of live pore forming bacterial protein toxin in a sample. The method includes: a) forming a membrane comprising a lipid and a receptor, b) contacting the membrane with an ion solution and the sample, c) measuring ion flow through the membrane, and d) comparing the ion flow to that of a control sample.

Another embodiment is directed toward kits for determining the amount of live pore forming bacterial toxin present in a sample. The kit includes: a lipid, an ion solution, receptor, and at least one of radio isotopes, dyes, and a system for measuring electric current.

Additional embodiments, objects and advantages of the invention will become more fully apparent in the detailed description below.

BRIEF DESCRIPTION OF THE DRAWINGS

The following detailed description will be more fully understood in view of the drawings in which.

Figure 1:
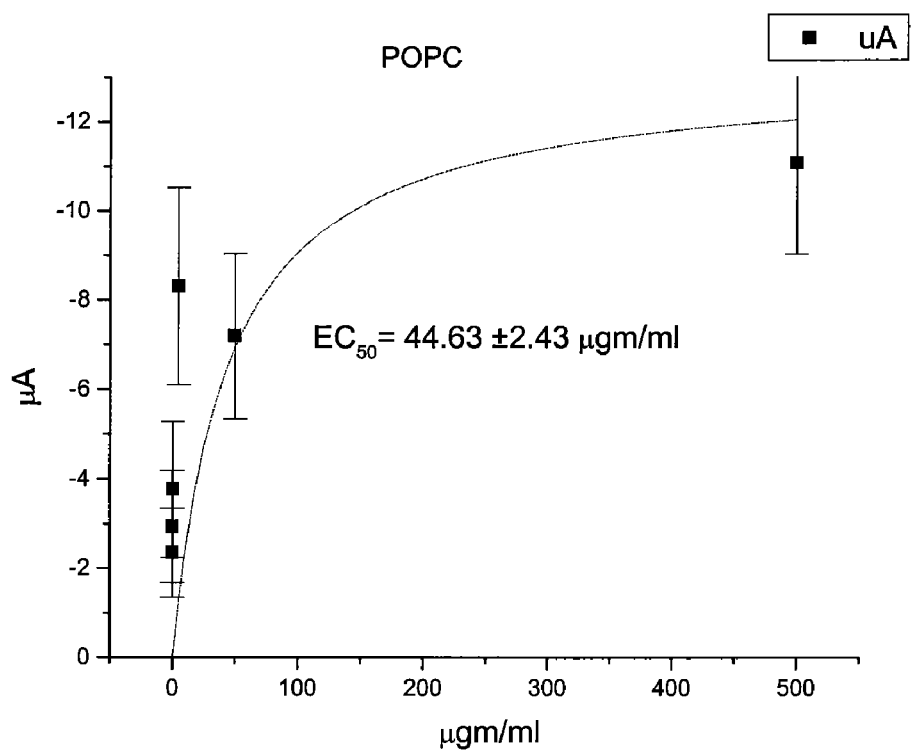
FIG. 1 is a graph depicting current flow across a membrane where no pore forming bacterial protein toxin or receptor is present.

The embodiments set forth in the drawings are illustrative in nature and are not intended to be limiting of the invention defined by the claims. Moreover, individual features of the drawing and the invention will be more fully apparent and understood in view of the detailed description.

DETAILED DESCRIPTION

Pore forming bacterial toxins can be both helpful and harmful. While the workings of pore forming bacterial protein toxins are generally known and have been generally described (see e.g. B. Geny and M. Popoff, *Bacterial protein toxins and lipids: pore formation or toxin entry into cells*, J. Biol. Cell (2006) 98, 667-678; which is incorporated herein by reference) until now, methods to assay these pore forming bacterial toxins and their receptors have been insufficient.

The present methods may, for example, be conducted as an in vitro assay which gives a measure of the ability of the protein to insert and form a pore, and which (when calibrated) can give a measure of the concentration of the toxin or the effective concentration of the toxin. Moreover, the methods of the present invention can be conducted by easy assembly of suitable components and can be miniaturized for detectors or used in high throughput screening.

Another advantage of the present methods is that the methods allow screening for either the pore forming bacterial protein toxin itself or for the receptor for the toxin. For example, if the pore forming bacterial protein toxin and the type of cells it attacks are known (human, for example), then differing types of human cells can be screened in the assay to determine which types of human cells have the receptor to which the known pore forming bacterial toxin will bind. Additionally, it is unnecessary to try and isolate the different receptors on each type of human cell prior to screening. The assay allows for the use of pieces of cell membranes from the target cells, which will include the receptors bound to the cell membranes, to screen for the receptor. Once the cell type containing the receptor for the pore forming protein toxin has been identified from the assay, then the receptors on the cell can be isolated and the specific binding receptor may be determined. In the reverse, when a cell is known to be attacked, pieces of that cell's membrane can then be used to determine the pore forming bacterial toxin protein which is attacking it.

Thus, one embodiment of the present invention is directed to methods for ionophorically screening bacterial protein toxins and receptors. The method includes: a) forming a membrane comprising a lipid and a receptor, b) contacting the membrane with the bacterial protein toxin and an ion solution, and c) measuring ion flow through the membrane.

Prior to using the above method, several compounds must be chosen. First, one must consider which compound the assay will be used to screen (i.e. the pore forming bacterial toxin protein or the receptor). There really is no limit to the pore forming bacterial compounds or receptors which can be screened with this assay. Some examples of pore forming bacterial toxins include: *staphylococcus, streptococcus pyogenes, listeria monocytogenesclostridium* prefringens, hemolysis, anthrax, etc. For some other examples, see the Geny and Popoff article incorporated by reference above. There are many more such pore forming bacteria which are known in the art. In fact, over one-third of all bacterial toxins have been identified as pore forming and thus would be impossible to list here. Additionally, this assay can be used to screen synthetic, genetically modified, or evolved species of pore forming bacterial toxins, as well as to identify bacterial toxins which were not previous known as being pore forming or were not previously known.

When selecting a lipid, any lipid or combination of lipids which will form a membrane which will allow the passage of ions through the membrane will work. The lipid, for example, may be natural, synthetic, from animals, from plants, from bacteria, from archeabacteria, etc. More specifically, in one embodiment, the lipid comprises a phospholipid. In a more specific embodiment, the lipid comprises at least one of 1-palmitoyl-2-oleoyl-sn-glycero-3-phosphocholine (POPC), 1-palmitoyl-2-oleoyl-sn-glycero-3-phosphoethanolamine (POPE), 1-palmitoyl-2-oleoyl-sn-glycero-3-phosphatidylserine (POPS), 1,2-diphytanoyl-sn-glycero-3-phosphocholine, and cholesterol. In a further embodiment, the lipid comprises POPC. In another embodiment, when the pore forming bacteria being screened comprises anthrax, then the lipid comprises 1,2-diphytanoyl-sn-glycero-3-phosphocholine. Some additional examples of lipids and methods to incorporate them into a membrane can be found in M. A. Dhoke, P. J. Ladha, F. J. Boerio, L. B. Lessard, D. H. Malinowska, J. Cuppoletti, and D. S. Wieczorek, *Porous membranes for reconstitution of ion channels*, Biochimica et Biophysica Acta 1716 (2005) 117-125, which is incorporated herein by reference.

Once the lipid and the receptor (or membrane containing the receptor) are chosen, then they can be combined to form the membrane. The lipid and the receptor will be applied to an appropriate substrate to allow formation of the membrane. The substrate can be any which will allow the formation of the membrane and ions to pass through the membrane. In one embodiment, the receptor and lipid are placed in a receptacle. In a further embodiment, the receptacle comprises a well. The receptacle can be adapted to allow for formation of the membrane. For example, according to one embodiment, an aperture is drilled in the receptacle to allow for the formation of a lipid bilayer which provides separation between two or more compartments.

In one embodiment, the lipid is suspended in a solution. According to a further embodiment, the lipid comprises POPC and is suspended in decane to allow formation of the membrane. In a specific embodiment, the POPC lipid is suspended in decane at a concentration of 40 mg/mL. In another embodiment, the receptor is suspended in an ion solution. According to one specific embodiment, the lipid in solution is combined with a mixture of the receptor and the ion solution to form the membrane. The ion solution is discussed further below. Depending on the lipid/receptor combination, the mixture may be required to sit for a certain amount of time before the membrane is formed. According to one embodiment, the amount of time required to form the membrane is selected from the group consisting of: 15 minutes, 30 minutes, 60 minutes, 90 minutes, 120 minutes, 150 minutes, and 180 minutes. Thus, in one embodiment, the membrane can form in as little as 15 minutes. The membrane is formed on an appropriate surface as discussed above.

Once the membrane is formed, the membrane is contacted with the selected pore forming bacterial toxin protein and an ion solution. In one embodiment, the selected protein contacts the membrane first. In another embodiment, the ion solution contacts the membrane first. In another embodiment, the bacterial toxin protein is added to the solution bathing the membrane. The ion solution, according to one embodiment, is a buffered physiological salt solution. There are no limitations to the types of ions used in the solution as long as they are permeable and do not inhibit the binding of the toxin to the receptor. There may be some proteins which have a specific need for a specific ion. This particular need would be known to one of skill in the art based on the selection of the protein. In one embodiment, the ion solution comprises potassium, chloride, magnesium, and/or calcium ions. In another embodiment, the ion solution comprises a combination of KCl, $CaCl_2$, and tris buffer. In a further embodiment, the ion solution comprises about 100 μM KCl, about 10 μM $CaCl_2$, and about 10 μM tris buffer. The ion solutions used in the membrane forming step can either be the same or different.

After the membrane is contacted with the selected protein and an ion solution, then the ion flow through the membrane can be measured. This can be accomplished by any suitable method. For example, suitable methods can include radio isotopes, dyes, and electric current. Thus, radio isotope exchange dyes which respond to membrane potential, or dyes which respond to specific ions could also be used to measure ion transport instead of electrical current. According to one embodiment, the method for measuring the ion flow through the membrane comprises measuring the electric current flowing through the membrane.

Measuring the concentration of the pore forming bacterial toxin as a function of the current allows the user to judge whether a pore has been formed in the membrane by the receptor/toxin pair. Thus, as shown in more detail in the examples below, adding the pore protein to a solution bathing a preformed protein produces a leak (electrical current) at higher concentrations than required when the pore protein is added to the solution bathing a membrane containing the receptors, which is similar to the dose dependence for adding and mixing the pore protein directly with the lipid before forming a membrane. This provides a way to determine the specificity of the interaction of the pore protein with the receptor. This also allows a way to determine the effective concentration of pore protein and to compare the ability of different pore proteins to interact with receptors or to compare the ability of a pore protein to interact with other receptors by measurement of the dose response for current flow and the maximum current flow.

In addition to the above general uses for screening bacterial toxins, the screening methods of the present invention can also be put into use in the crop industry. Often, farmers, use insecticides as a method for trying to protect crops. Unfortunately, insects often develop immunity to the types of insecticides used and thus new ones need to be continually developed. Current methods of developing insecticides require that dead insects be collected, their gastric contents be isolated, the bacteria in the gut be tested to determine what killed the insect, and then the bacteria's pore protein be isolated. The current assay technique is an improvement over the previous method because it allows for the screening of a large number of pore forming bacterial toxins with only the cell membranes of the target insects.

Therefore, another embodiment of the present invention is directed to methods for ionophorically screening a selected protein for insect toxicity. Unlike previous methods which required testing of insecticides upon the insects themselves, Applicant has discovered that the efficacy of insecticides can be tested in the lab using a less expensive and time saving method. This method includes: a) forming a membrane comprising a lipid and an insect receptor, b) contacting the membrane with a pore forming bacterial protein toxin and an ion solution, and c) measuring ion flow through the membrane. In one embodiment, the insect receptor protein is in the form of a solution comprising membranes from insect cells. This method can be further expounded upon in light of the discussion above.

In addition to the use for screening insecticides, one embodiment of the present invention can also be used to determine the live amount of a bacterial toxin in a sample. This method includes: a) forming a membrane comprising a lipid and an receptor, b) contacting the membrane with an ion solution and the sample, c) measuring ion flow through the membrane, and d) comparing the ion flow to that of a control of the sample. For example, in one embodiment, the above method can be used to screen for the amount of live anthrax in a sample. One of the receptors which can be used with anthrax is capillary morphogenesis 2 (CMG2). If an area became contaminated with anthrax, the above method can be used to determine the amount of anthrax in the room and after cleanup can be used to determine whether there is still any live anthrax remaining in the room by comparing the ion flow of the sample in the room to a control measurement of ion flow for anthrax. Thus, a standard curve using a set amount of receptor is established, and a standard curve for current flow is established as in the examples.

There is a dose dependence for induction of current flow that is characteristic for the toxin and a maximal current that is characteristic for the amount of receptor and the pore protein. The sample can be tested at various concentrations for ability to induce a current and for the ability to give a maximal current under those same conditions. The dose response and the maximal response is directly proportional to the concentration of the toxin. If the pore protein is modified by design or conditions, the effective (rather than absolute) amount of the toxin is measured. Various practical embodiments of this method will be apparent to one of ordinary skill in the art in light of the discussion above.

Additionally, the components of the above methods for screening pore forming bacterial toxin protein compounds may be contained in a kit. These kits are useful for example, by law enforcement to test for pore forming bacterial toxin proteins which may be used in germ warfare. Such toxins include, for example, anthrax. In one embodiment, the kits of the invention includes: a lipid, an ion solution, a receptor, and at least one of radio isotopes, dyes, and a system for measuring electric current. In one embodiment, this measuring system includes electrodes and a meter, although, additional components may also be included. In a further embodiment, the kits according to the invention also include instructions for their use and a guide with control values for pore forming bacterial compounds which could be used for germ warfare. Suitably, the kit may include a receptacle, for example, wells, providing a substrate for membrane formation. Inhibitors of ion flow (such as tetrabutyl ammonium chloride) in the case of anthrax protective antigen could also be included to show the specificity of the response. Additionally, a control using another receptor (for example, red blood cell membranes) to show that the response is specific for the anthrax receptor would be useful to sort and exclude false positives. A positive response (such as using hemolysin bacterial protein with the detector) could be included to show that the device was responding properly. In one embodiment, a system for standardizing the anthrax pore protein-anthrax receptor under the conditions of the test is included. Additionally, a system determination of the dose response of the pore protein when added without toxin can be incorporated to demonstrate the specificity of interaction with the pore. Moreover, a system to determine the dose response when the pore protein is directly mixed with lipid can be used to demonstrate that the pore protein behaves under the standard conditions as originally tested. Other variations, including multiple assays under each condition, can be used to evaluate possible false negatives or false positives. Various additional embodiments of this method, within the scope of the invention, will be further apparent to one of skill in the art in light of the discussion above.

EXAMPLES

Figure 2:
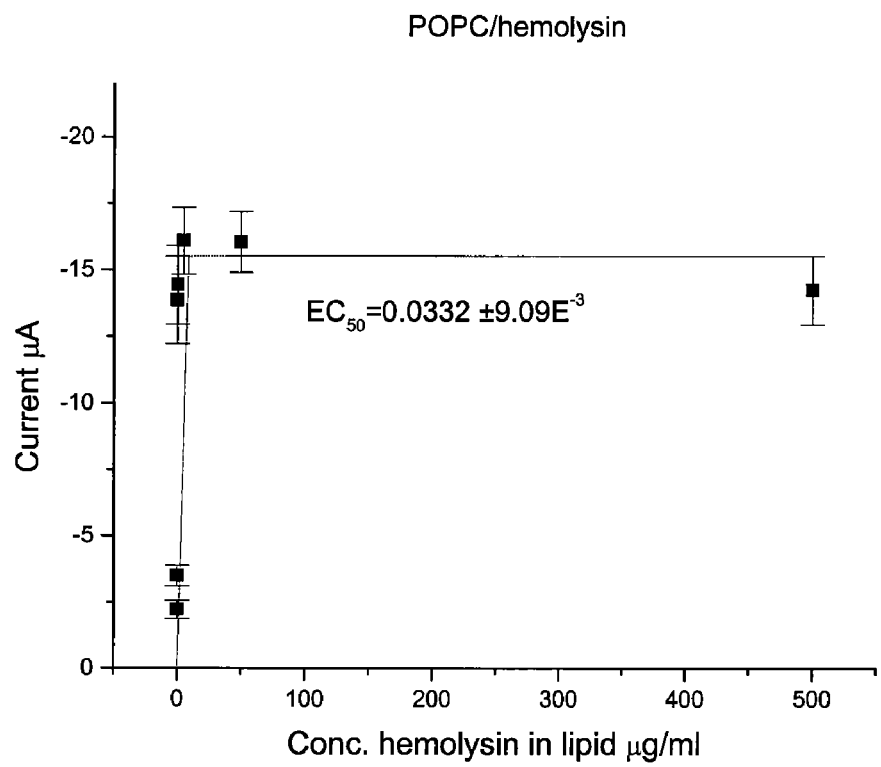
FIG. 2 is a graph depicting current flow across a membrane versus concentration of hemolysin where no receptor is present.
Figure 3:
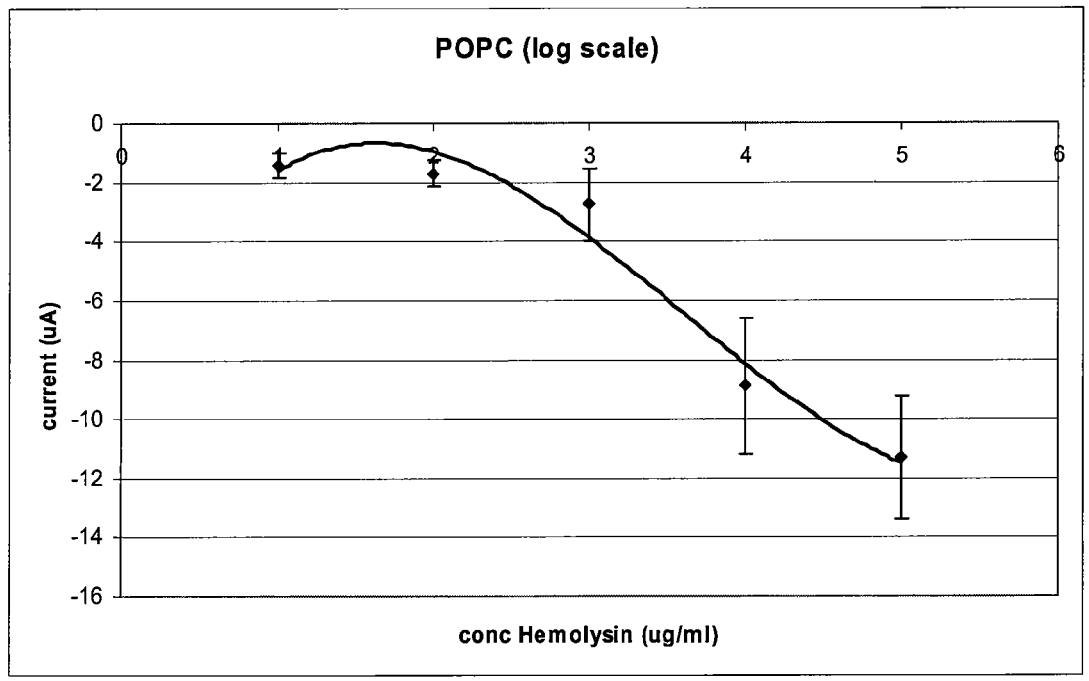
FIG. 3 is a graph depicting in log scale current flow across a membrane versus concentration of hemolysin where no receptor is present in the membrane.

A control test involves adding a range of concentrations of hemolysin in solution to pre-formed bilayer cups. These cups are adapted from the wells in a 96 well plate. To certain of these cups/wells, one 50 micron hole is laser drilled through the bottom of the well to form an aperture suitable for forming a membrane. A lipid layer is formed on the top surface of each cup by pipetting in 7 µL of POPC having a 40 mg/mL concentration in decane. An ion solution is formed comprising 100 µM KCl, about 10 µM CaCl$_2$, and about 10 µM tris buffer. The ion solution is added to the well followed by the addition of varying concentrations of hemolysin. The concentrations range from about 0 to about 500 mg/mL. Once the hemolysin solution is added, the current flow across the membrane as a function of hemolysin concentration is measured using P-clamp 5.0 software application and the associate test fixture. The results are shown in FIG. 2-3.

Figure 4:
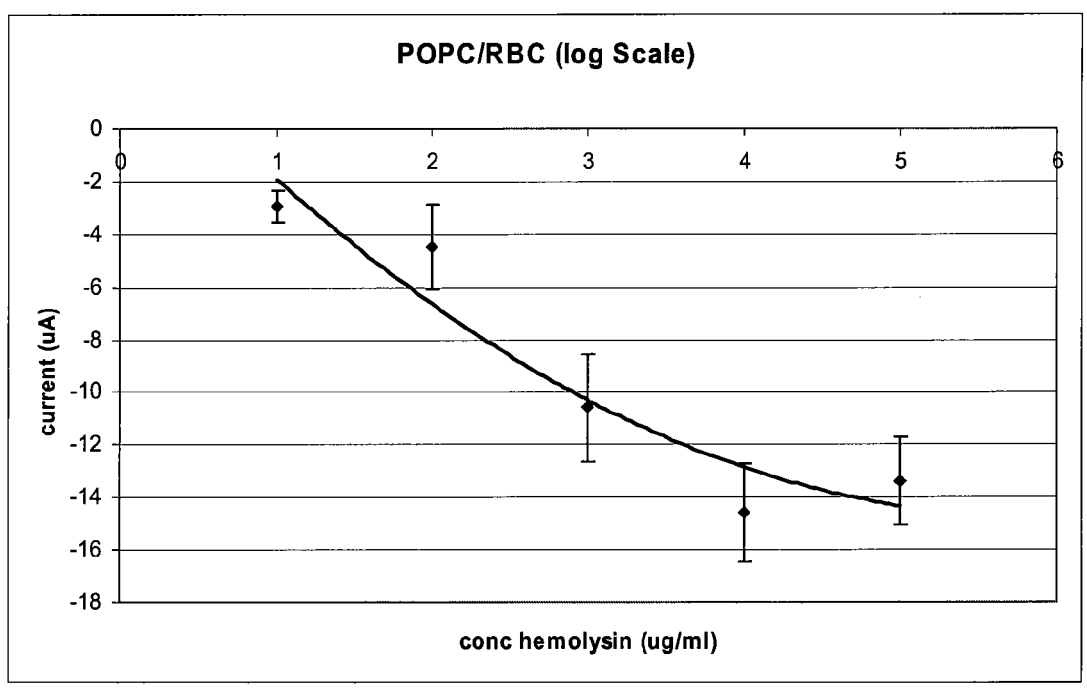
FIG. 4 is a graph depicting in log scale current flow across a membrane versus concentration of hemolysin where a receptor is present in the membrane
Figure 5:
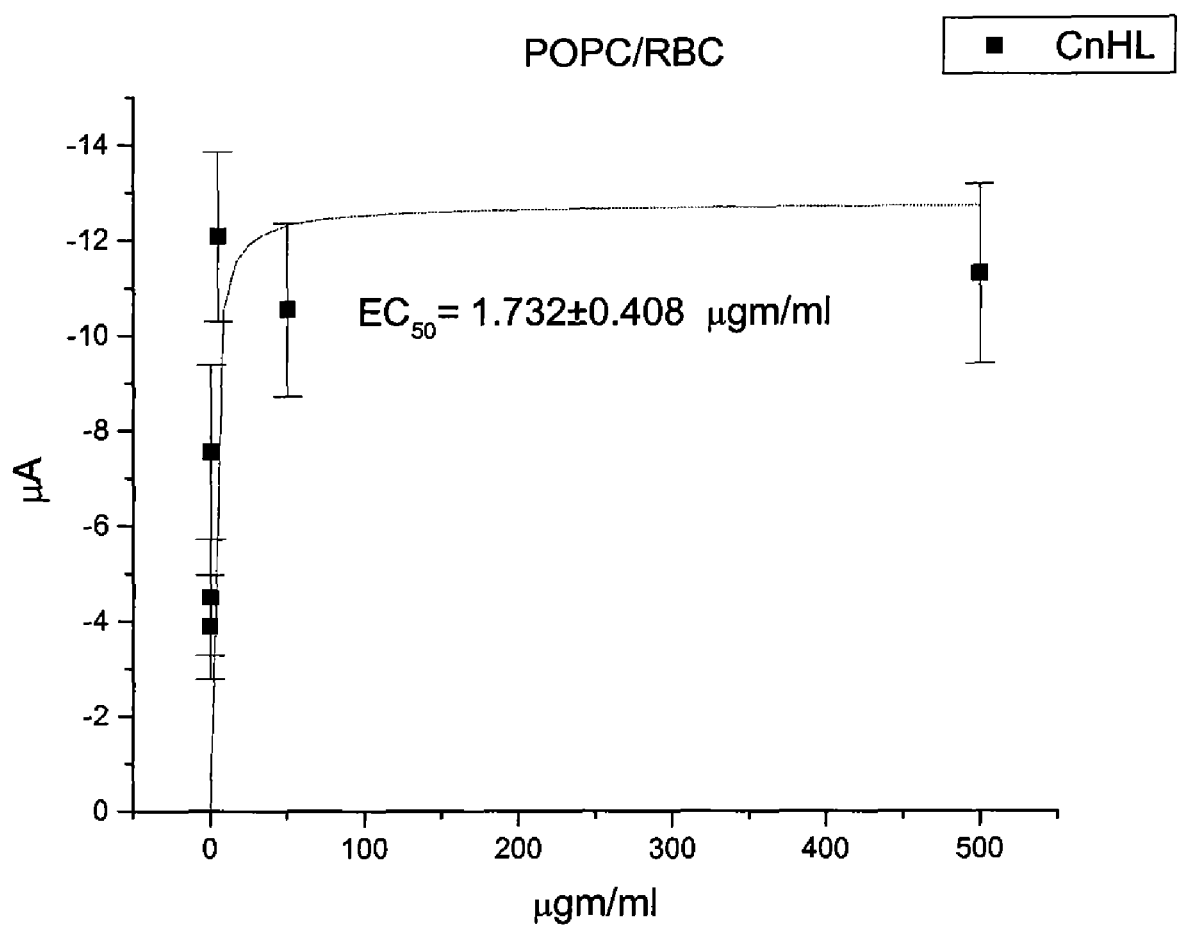
FIG. 5 is a graph depicting current flow across a membrane versus concentration of hemolysin where a receptor is present in the membrane.

Once the control test is completed, the experiment is repeated for the same range of hemolysin concentrations, except that the lipids forming the membrane are mixed with membranes from red blood cells (which include the insect receptor protein). The red blood cell membranes are obtained by lysis N (0.15 M NH$_4$Cl, 10 µM KCo$_3^-$, and 0.1 µM EDT.) The membranes are collected by centrifugation. One milliliter of red blood cell membranes is resuspended in the ion solution listed above. Then, 5 µL if the resuspended cell membranes are pipetted into each well. One hour of time is allowed to pass, then 100 µL of the ion solution is added, followed closely by the range of hemolysin concentrations as used in the control experiment. The current through the membrane is measured as before and plated versus concentration as seen in FIG. 4-5.

Figure 6:
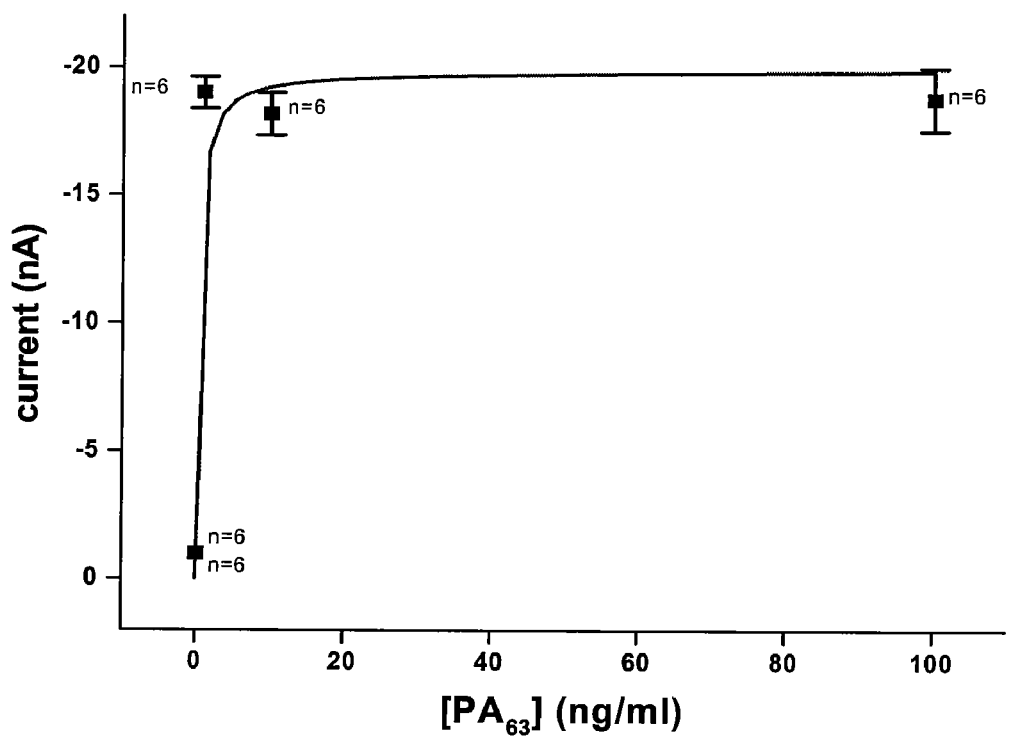
FIG. 6 is a graph depicting the current flow across a membrane versus concentration of protective antigen 63.

In another example, 3% (w/w) 1,2-Diphytanoyl-sn-glycero-3-phosphocholine lipid solution is placed into wells on a 96 well plate with 50 micron laser drilled holes. Protective antigen 63 (1000 µg/ml stock solution diluted 1:10 until a final concentration of 0.1 ng/ml with sterile water) is used. The protective antigen is allowed to incubate for 30 minutes. 100 mM KCl/10 mM CaCl$_2$/10 mM Tris, pH=7.1-7.4 is the salt solution added. The plate is then placed into a bath which contains the same neutral salt solution buffer and allowed to incubate for an additional 60 minutes. The current is measured using PCLAMP. As shown in FIG. 6, the EC$_{50}$ value is determined to be 0.32±0.24 ng/ml.

Figure 7:
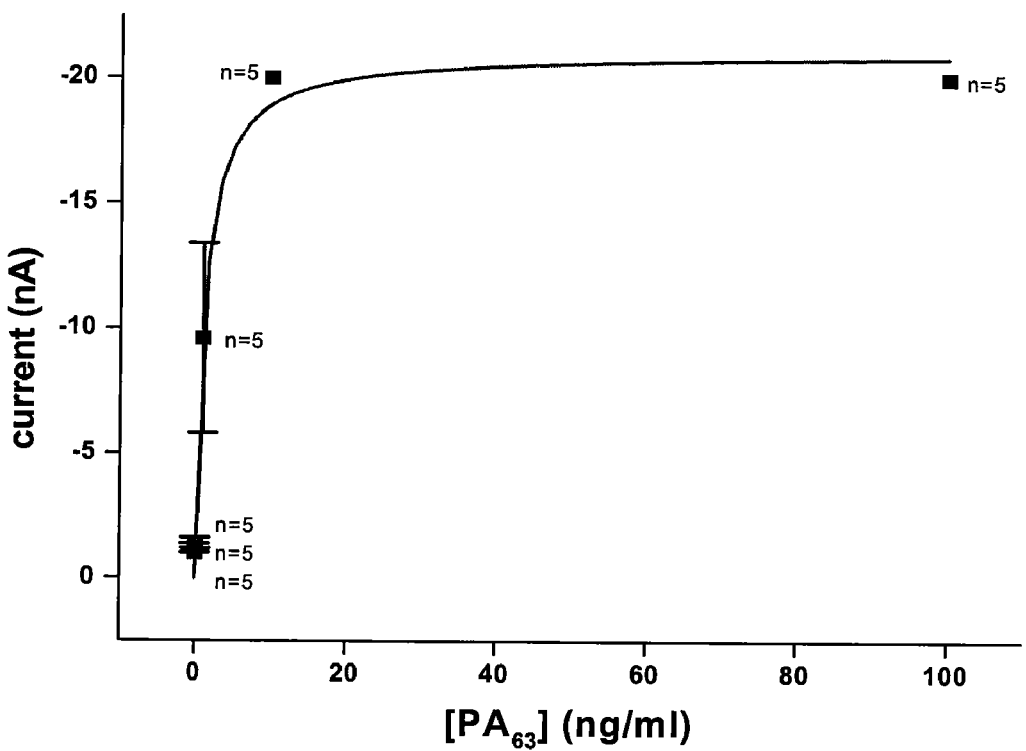
FIG. 7 is a graph depicting the current flow across a membrane versus concentration of protective antigen 63 dissolved in 3% (w/w) 1,2-Diphytanoyl-sn-glycero-3-phosphocholine lipid with and incubation time of 1.5 hours.

In a further example, protective antigen 63 (1000 µg/ml stock) dissolved in 1,2-Diphytanoyl-sn-glycero-3-phosphocholine lipid is added to in a 96 well plate with 50 micron laser drilled holes. The bilayer and protective antigen 63 are allowed to settle for 15 minutes. 100 mM KCl/10 mM CaCl$_2$/10 mM Tris, pH=7.1-7.4 is the salt solution used in the wells. The plate is placed into a 100 mM KCl/10 mM CaCl$_2$/10 mM Tris, pH=5.2-5.5 buffer bath and allowed to incubate for 60 minutes. The plate is then removed from the buffer bath and allowed to incubate for an additional 30 minutes and the plate is then placed back into the acidic salt solution. The current is measured using PCLAMP. As shown in FIG. 7, the EC$_{50}$ is determined to be 1.01±0.23 ng/ml.

Figure 8:
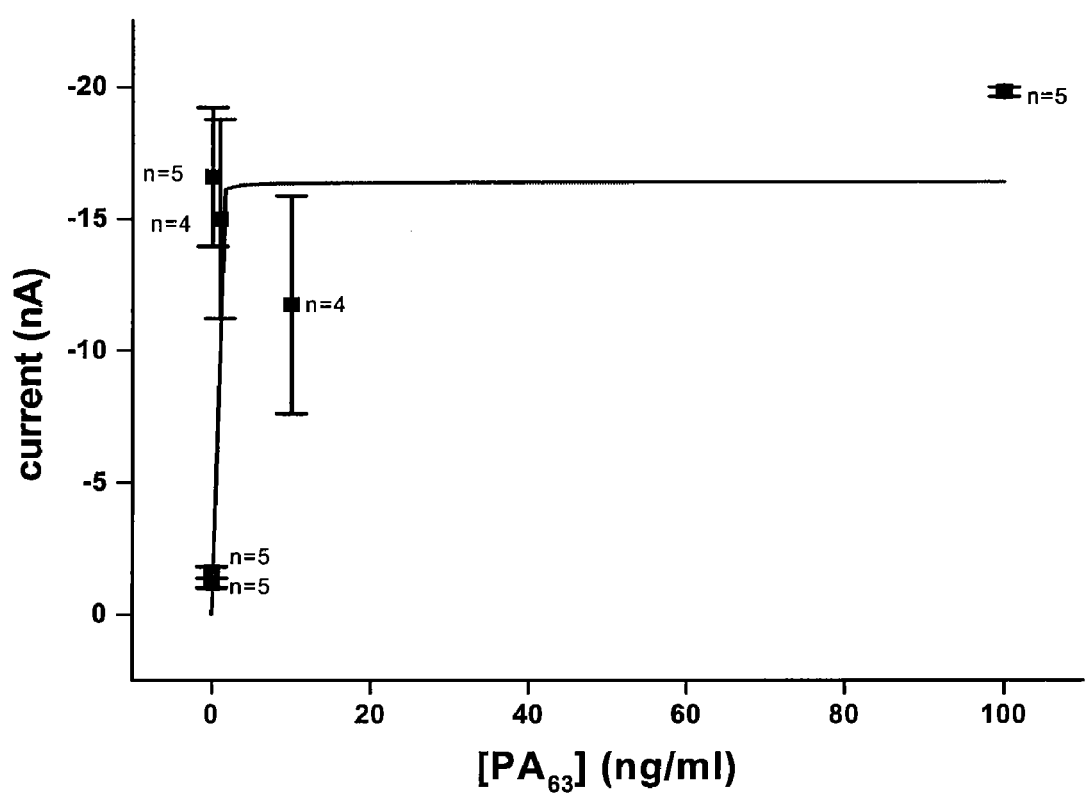
FIG. 8 is a graph depicting the current flow across a membrane with CHO-K1 cell membrane vesicles versus the concentration of protective antigen 63 with an incubation time of 1.5 hours.

In an additional example, 3% (w/w) 1,2-Diphytanoyl-sn-glycero-3-phosphocholine is place in the 96 well plate with 50 micron laser drilled holes. CHO-K1 cell membrane vesicles are added to the lipid bilayer. Interaction of the bilayer and vesicles is allowed to occur over a 1 hour period, with the plate uncovered. 100 mM KCl/10 mM CaCl$_2$/10 mM Tris, pH=7.1-7.4 salt solution is then added to the wells. The plate is then placed into a 100 mM KCl/10 mM CaCl$_2$/10 mM Tris, pH=5.2-5.5 buffer bath and the ions are allowed to equilibrate for 15 minutes. The bilayers are then tested for stability and to see if the bilayers are closed. Protective antigen 63 (1000 µl/ml stock) is then added and allowed to incubate for 1.5 hours. Then more neutral salt solution is added and the plate is placed into the acidic salt solution. The current is measured immediately using PCLAMP. As shown in FIG. 8, the EC$_{50}$ is determined to be 0.028±0.028 ng/ml.

Figure 9:
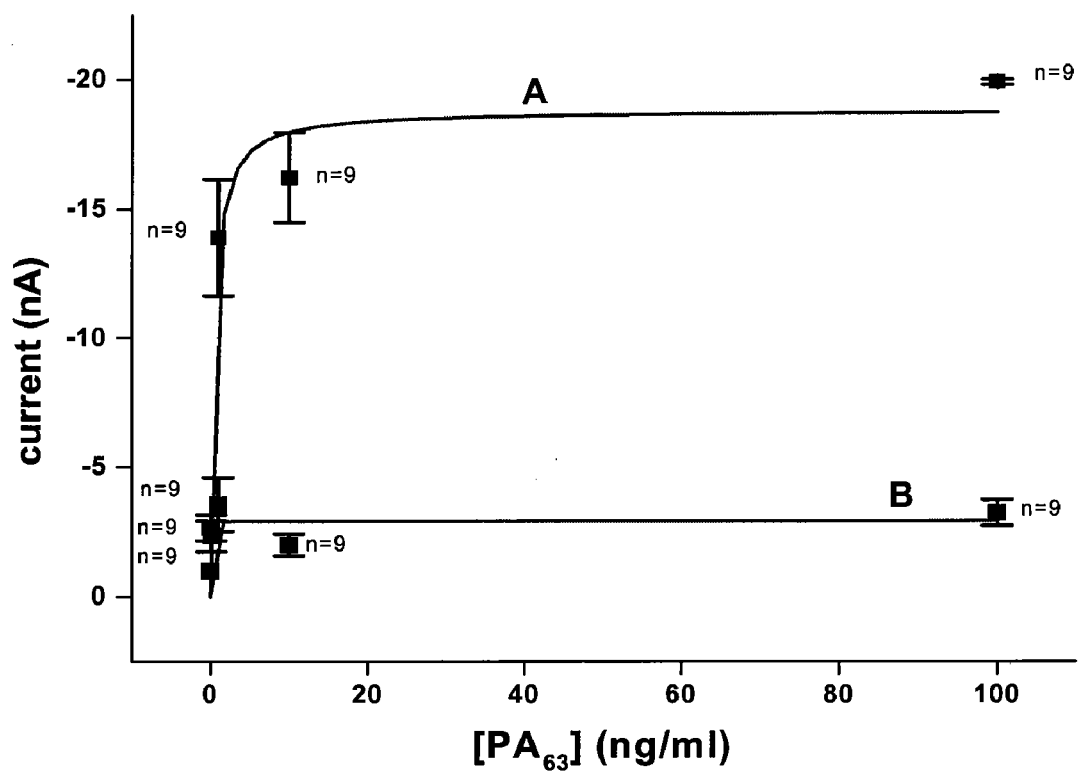
FIG. 9 is a graph depicting the current flow across a membrane versus concentration of protective antigen 63.

As another example, a final concentration of 50 mM tetrabtylammonium chloride (500 mM stock) is added to the wells in order to inhibit any protective antigen 63 pores that may have formed. In FIG. 9, line A depicts the Lipid bilayer+protective antigen 63 whose V$_{max}$ is determined to be −18.80±1.21 nA and line B depicts Lipid bilayer+protective antigen 63+tetrabutylammonium chloride whose V$_{max}$ value is determined to be −2.91±0.54 nA. (P<0.0005 when comparing the V$_{max}$ values for the uninhibited protective antigen 63 versus the inhibited protective antigen 63.)

Figure 10:
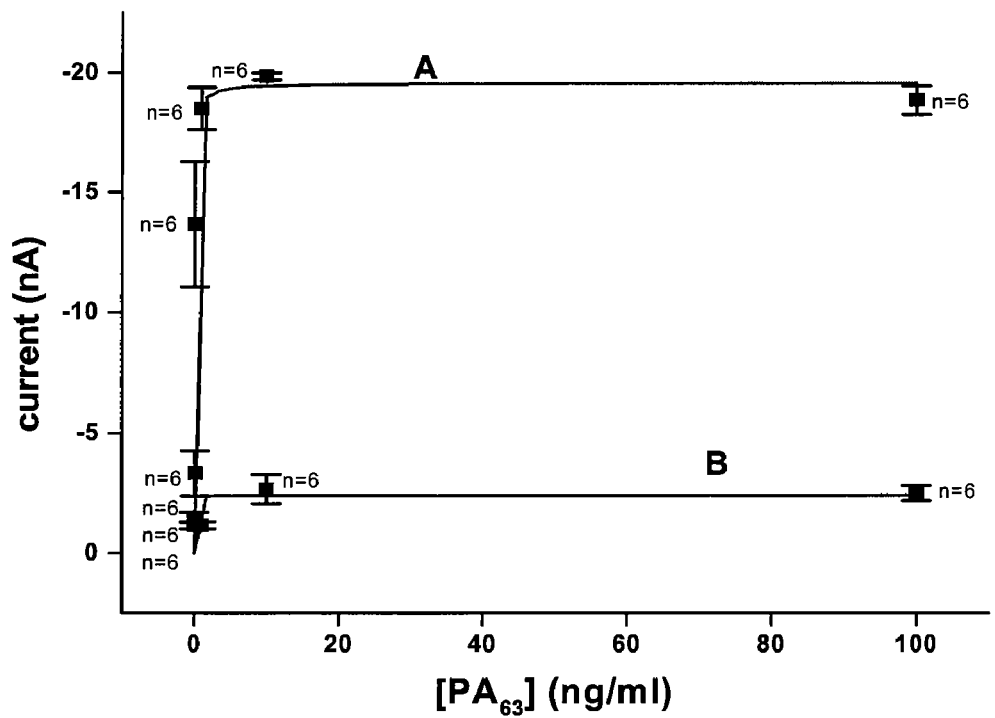
FIG. 10 is a graph depicting the inhibition of protective antigen 63 dissolved in 3% (w/w) 1,2-Diphytanoyl-sn-glycero-3-phosphocholine.

In another example, as shown in FIG. 10, a final concentration of 50 mM tetrabutylammonium chloride (500 mM stock) is added to the wells in order to inhibit any protective antigen that may have formed pores in the lipid bilayer. Line A shows protective antigen 63 dissolved in 3% (w/w) 1,2-Diphytanoyl-sn-glycero-3-phosphocholine whose V$_{max}$ is determined to be −19.54±0.71 nA. Line B shows protective antigen 63 dissolved in 3% (w/w) 1,2-Diphytanoyl-sn-glycero-3-phosphocholine+tetrabutylammonium chloride whose V$_{max}$ is determined to be −2.41±0.55 nA. (P<0.0005 when comparing the uninhibited protective antigen 63 against the inhibited protective antigen 63.)

Figure 11:
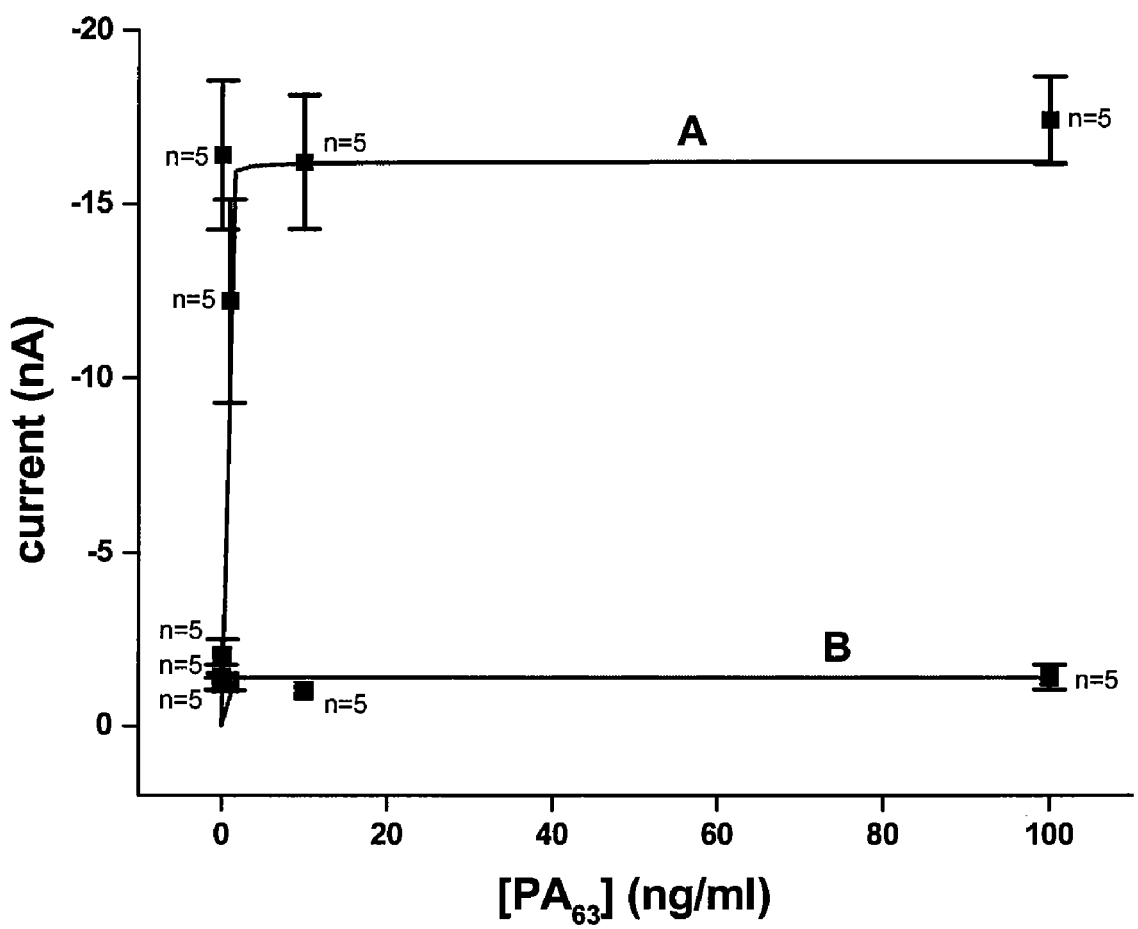
FIG. 11 is a graph depicting the inhibition of the membrane with CHO-K1 cell membrane vesicles and protective antigen 63.

In yet another example, as shown in FIG. 11, a final concentration of 50 mM tetrabtylammonium chloride (500 mM stock) is added to the wells in order to determine if pore formation occurred. Line A shows Lipid bilayer+CHO-K1 cell membrane vesicles+protective antigen 63 whose V$_{max}$ is determined to be −16.20±1.82 nA. Line B shows Lipid bilayer+CHO-K1 cell membrane vesicles+protective antigen 63+tetrabutylammonium chloride whose V$_{max}$ is determined to be −1.39±0.41 nA. (P<0.0005 when comparing the V$_{max}$ of the uninhibited protective antigen 63 to the inhibited protective antigen 63.)

Figure 12:
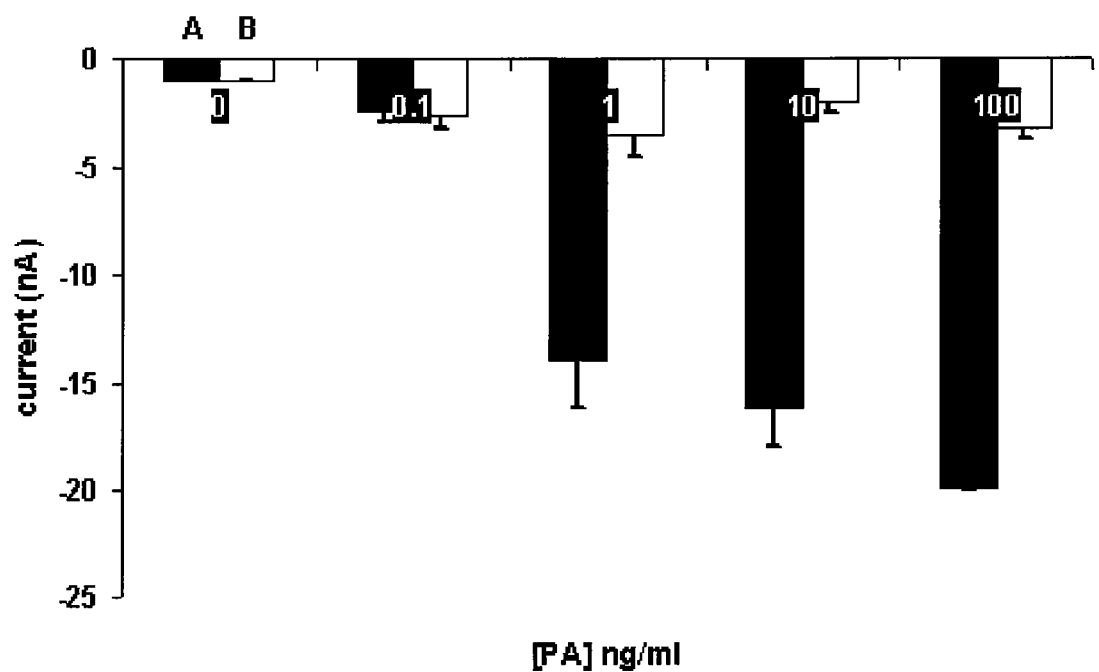
FIG. 12 is a graph depicting the inhibition of the membrane and protective antigen 63.

In another example, shown in FIG. 12, inhibition of lipid bilayer+protective antigen 63 is shown. Column A shows Lipid bilayer+protective antigen 63 without 50 mM (final concentration) of tetrabutylammonium chloride (black). Column B shows Lipid bilayer+protective antigen 63 with 50 mM (final concentration) of tetrabutylammonium chloride for inhibition (white). (n=9)

Figure 13:
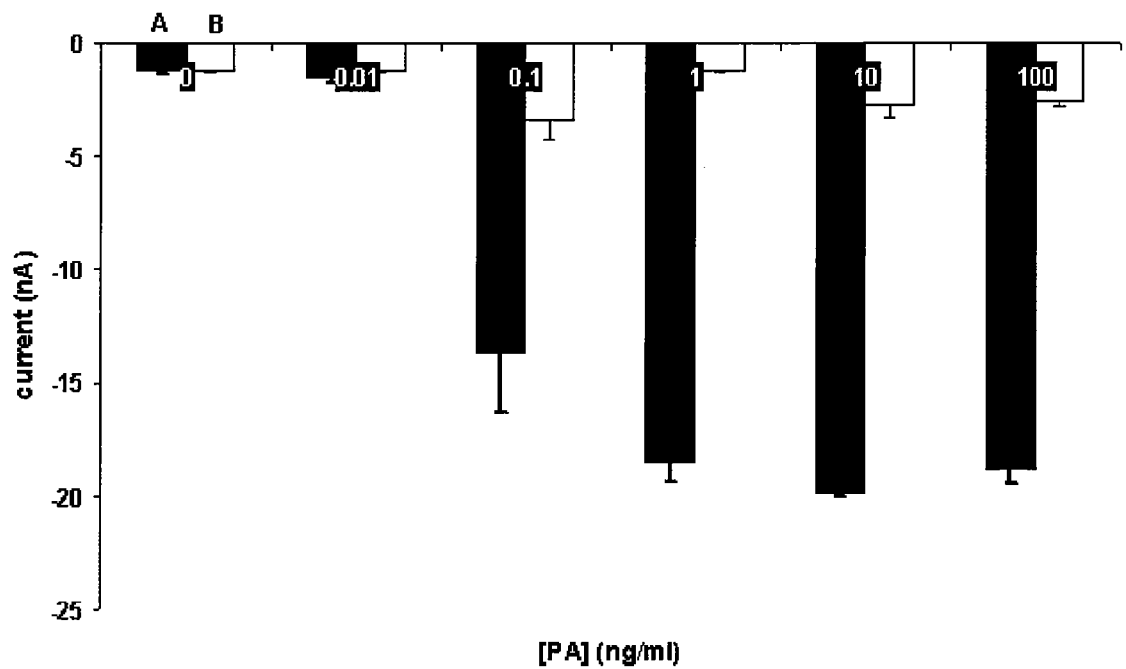
FIG. 13 is a graph depicting the inhibition of protective antigen 63 dissolved in 3% (w/w) 1,2-Diphytanoyl-sn-glycero-3-phosphocholine.

In another example, as shown in FIG. 13, shows inhibition of protective antigen 63 dissolved in 3% (w/w) 1,2-Diphytanoyl-sn-glycero-3-phosphocholine. Column A shows Protective antigen 63 dissolved in 3% (w/w) 1,2-Diphytanoyl-sn-glycero-3-phosphocholine without 50 mM (final concentration) tetrabutylammonium chloride (black). Column B shows Protective antigen 63 dissolved in 3% (w/w) 1,2-Diphytanoyl-sn-glycero-3-phosphocholine with 50 mM (final concentration) tetrabutylammonium chloride for inhibition (white). (n=6)

Figure 14:
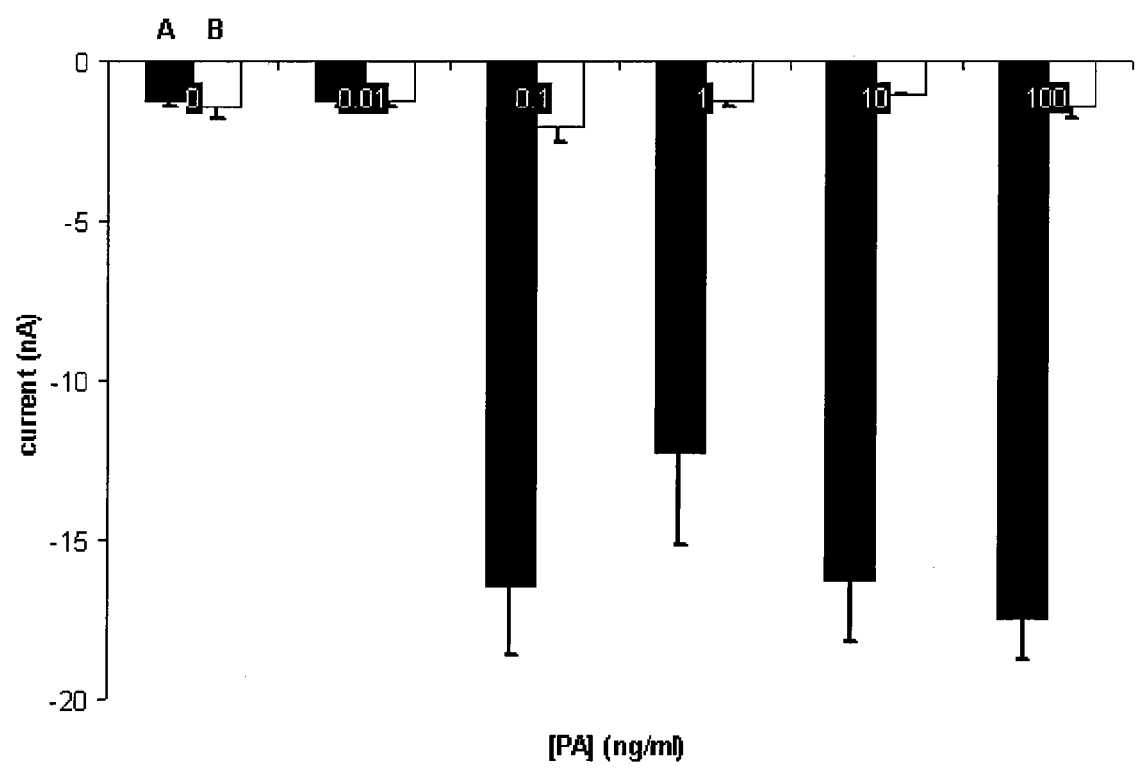
FIG. 14 is a graph depicting the inhibition of the membrane with CHO-K1 cell membrane vesicles and protective antigen 63.

As seen in another example, FIG. 14, inhibition of lipid bilayer+CHO-K1 cell membrane vesicles+protective antigen 63 is shown. Column A shows Lipid bilayer+CHO-K1 cell membrane vesicles+protective antigen 63 without 50 mM (final concentration) tetrabutylammonium chloride (black). Column B shows Lipid bilayer+CHO-K1 cell membrane vesicles+protective antigen 63 with 50 mM (final concentration) tetrabutylammonium chloride for inhibition (white). (n=5)

FIGS. 6-14 show results with studies of anthrax protective antigen. As shown in FIG. 6, the anthrax protective antigen in the absence of receptor but added to the solution bathing a lipid membrane gives an effective concentration (EC$_{50}$) of forming a pore of 1.01±0.23 ng/ml. As shown in FIG. 7, mixing pore protein with lipid prior to forming the lipid bilayer gives an EC$_{50}$ of 0.32±0.24 ng/ml, much lower than for the condition shown in FIG. 6. As shown in FIG. 8, adding pore protein to the solution bathing lipid bilayer containing the receptor membranes gives an EC$_{50}$ of 0.028±0.028 ng/ml.

This value is much lower than when the pore protein is added to a membrane lacking the receptor membranes, and is a measure of the ability of the receptor to reduce the concentration of pore protein that is required to form a pore in the membrane. The $EC_{50}$ is also lower than even mixing the protein with the lipid alone, suggesting that the receptor-pore protein pair is highly effective in reducing the concentration of pore protein that is inserted in the membrane. As shown in FIG. 9, tetrabutyl ammonium chloride, a known inhibitor of ion flow through the anthrax pore protein completely blocks current flow, demonstrating the specificity of the pore protein in eliciting a current. FIG. 10 shows that the anthrax pore (protective antigen) is also blocked by tetrabutyl ammonium chloride and FIG. 11 shows that the receptor-pore protein complex is also blocked. Thus, the specificity of the pore formation can be so demonstrated using appropriate inhibitors. FIGS. 12-14 show that that the pore added to the solution bathing a lipid membrane, pore mixed with the lipid before formation, and the pore receptor complex produce ion currents in a dose dependent manner and the currents can be blocked by tetrabutyl ammonium chloride.

As shown in greater detail in FIGS. 1-17 and the examples described above, the method of the present invention demonstrates about two orders of magnitude of greater sensitivity in detecting the presence of the test compound in comparison with a membrane without a receptor. In particular, for a given desired current, the method of the invention achieves this current at about $\frac{1}{100}^{th}$ of the concentration of the control.

The foregoing description of various embodiments and principles of the invention has been presented for the purposes of illustration and description. It is not intended to be exhaustive or to limit the inventions to the precise forms disclosed. Many alternatives, modifications, and variations will be apparent to those skilled the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and scope of the inventions as defined by the claims.

What is claimed is:

1. A method for ionophorically screening pore forming bacterial protein toxins and receptors for insect toxicity, comprising:
   a) forming a membrane in a receptacle comprising an aperture by combining a lipid bilayer and an insect receptor, such that the membrane forms across the aperture and provides separation between two compartments in the receptacle,
   b) contacting the membrane with an ion solution and a pore forming bacterial protein toxin, whereby the pore forming bacterial protein toxin binds the insect receptor and forms a pore in the membrane, and
   c) measuring ion flow through the pore in the membrane, wherein the lipid bilayer comprises at least one of 1-palmitoyl-2-oleoyl-sn-glycero-3-phosphocholine (POPC), 1-palmitoyl-2-oleoyl-sn-glycero-3-phosphoethanolamine (POPE), 1-palmitoyl-2-oleoyl-sn-glycero-3-phosphatidylserine (POPS), 1,2-diphytanoyl-sn-glycero-3-phosphocholine, and cholesterol.

2. The method of claim 1, wherein the ion in the ion solution is selected the group consisting of: Ca, K, Cl, Mg, and combinations thereof.

3. The method of claim 1, wherein the insect receptor is in the form of a solution comprising membranes from insect cells.

4. The method of claim 1, wherein the act of measuring ion flow through the membrane is accomplished by at least one of radio isotopes, dyes, and measuring electric current.

5. The method of claim 1, wherein the lipid bilayer comprises POPC.

6. The method of claim 1, wherein the ion solution comprises a buffered physiological salt solution.

* * * * *